(12) United States Patent
Chien

(10) Patent No.: US 9,395,560 B2
(45) Date of Patent: Jul. 19, 2016

(54) PROGRESSIVE MULTIFOCAL OPHTHALMIC LENS

(71) Applicant: Pegavision Corporation, Guishan Township, Taoyuan County (TW)

(72) Inventor: Pai-Hung Chien, Guishan Township, Taoyuan County (TW)

(73) Assignee: Pegavision Corporation, Guishan Township (TW)

( * ) Notice: Subject to any disclaimer, the term of this patent is extended or adjusted under 35 U.S.C. 154(b) by 134 days.

(21) Appl. No.: 14/452,831

(22) Filed: Aug. 6, 2014

(65) Prior Publication Data

US 2015/0316790 A1    Nov. 5, 2015

(30) Foreign Application Priority Data

Apr. 30, 2014    (TW) .............. 103207543 U

(51) Int. Cl.
| | |
|---|---|
| *G02C 7/00* | (2006.01) |
| *G02C 7/02* | (2006.01) |
| *G02C 7/06* | (2006.01) |
| *G02C 7/04* | (2006.01) |
| *A61F 2/16* | (2006.01) |

(52) U.S. Cl.
CPC .............. *G02C 7/063* (2013.01); *A61F 2/1618* (2013.01); *G02C 7/042* (2013.01); *G02C 7/045* (2013.01); *A61F 2/1637* (2013.01)

(58) Field of Classification Search
CPC ........ G02C 7/063; G02C 7/042; G02C 7/045; A61F 2/1618; A61F 2/1637

USPC ............... 359/718, 720; 351/159.41–159.54, 351/159.06, 159.12; 623/6.24
See application file for complete search history.

(56) References Cited

U.S. PATENT DOCUMENTS

| | | | | |
|---|---|---|---|---|
| 5,173,723 A | * | 12/1992 | Volk ...................... | A61F 2/1613 351/159.47 |
| 6,899,425 B2 | * | 5/2005 | Roffman ................ | G02C 7/028 351/159.21 |
| 2005/0088615 A1 | | 4/2005 | Roffman et al. | |

FOREIGN PATENT DOCUMENTS

| | | |
|---|---|---|
| EP | 0107444 A2 | 5/1984 |
| GB | 2364136 A | 1/2002 |
| WO | 9206400 A1 | 4/1992 |
| WO | 2009017403 A1 | 2/2009 |

* cited by examiner

*Primary Examiner* — Scott J Sugarman
*Assistant Examiner* — Mustak Choudhury
(74) *Attorney, Agent, or Firm* — Hayes Soloway, P.C.

(57) ABSTRACT

A progressive multifocal ophthalmic lens includes at least three high power segments, at least three low power segments, and a plurality of progressive power segments. Shapes of the high power segments and the low power segments are sectors. The high power segments and the low power segments are disposed alternately along an arc direction of the progressive multifocal ophthalmic lens. Shapes of the progressive power segments are sectors. Two sides of each of the progressive power segments along the arc direction respectively connect one of the high power segments and one of the low power segments. The high power segments, the low power segments, and the progressive power segments form a progressive multifocal surface.

9 Claims, 10 Drawing Sheets

PROGRESSIVE MULTIFOCAL OPHTHALMIC LENS

RELATED APPLICATIONS

This application claims priority to Taiwan Application Serial Number 103207543, filed Apr. 30, 2014, which is herein incorporated by reference.

BACKGROUND

1. Field of Invention

The present invention relates to a progressive multifocal ophthalmic lens.

2. Description of Related Art

An ophthalmic lens is a lens worn on a cornea or in an eye for correcting the power of a patient with ametropia. For a patient with an astigmatism, myopia, or hyperopia, wearing an ophthalmic lens should correct both ametropia and astigmatism simultaneously. However, due to the directional ability of an astigmatic eye, an astigmatic ophthalmic lens has a fixed axis relative to the eye, such that an astigmatic ophthalmic lens worn by the patient must have a stabilization design to prevent it from rotating. The stabilization design may cause increased lens thickness, which often results in low oxygen-permeability, high abnormal sensation, or low wearing comfort, or may require more time to be stable. Moreover, the ophthalmic lens needs to be prescribed again if the axis of the ophthalmic lens over shifts relative to the astigmatic axis of the eye. Manufacturing companies must therefore prepare at least 18 different ophthalmic lenses with a single power and 18 axes from 0 degrees to 180 degrees. These ophthalmic lenses require significant inventory, and create increased management pressure, both of which are inconvenient for manufacturing companies.

Moreover, most of the presbyopia lenses on the market are aspherical designs with axis symmetry and progressive power, or are concentric design with alternate distance- and near-visual segments. These two designs primarily dependent on the size of the pupil. Since the size of the pupil changes with the ambient light intensity, contrast, or ages of the patient, and the size-adjustment ability of the pupil decreases as the wearer's age increases, it becomes more difficult to adjust the pupil size for converting between the distance-vision and the near-vision, especially for an eye with huge difference between the ability to see near or far.

SUMMARY

An aspect of the present invention is to provide a progressive multifocal ophthalmic lens including at least three high power segments, at least three low power segments, and a plurality of progressive power segments. Shapes of the high power segments and the low power segments are sectors. The high power segments and the low power segments are disposed alternately along an arc direction of the progressive multifocal ophthalmic lens. Shapes of the progressive power segments are sectors. Two sides of each of the progressive power segments along the arc direction respectively connect one of the high power segments and one of the low power segments. The high power segments, the low power segments, and the progressive power segments form a progressive multifocal surface satisfying the following relationships:

when $[180°\cdot(2s-2)]/p < \theta < [180°\cdot(2s-1)]/p$, $$Z_1(r,\theta) = R - \sqrt{R^2 - r^2} + \left(\sum_{n=1}^{m} a_n \cdot r^n\right) \cdot \left[\cos\left[\pi \cdot \left(\frac{p\cdot\theta}{180}\right)^q\right] - 1\right]; \text{ and}$$

when $[180°\cdot(2s-1)]/p < \theta < (180°\cdot 2s)/p$, $$Z_2(r,\theta) = R - \sqrt{R^2 - r^2} + \left(\sum_{n=1}^{m} a_n \cdot r^n\right) \cdot \left[\cos\left[\pi \cdot \left(2 - \frac{p\cdot\theta}{180}\right)^q\right] - 1\right],$$

where r is a radial coordinate of the progressive multifocal surface, $0 \leq r \leq r_0$. $r_0$ is the radius of an optical segment of the progressive multifocal surface. $\theta$ is an angular coordinate of the progressive multifocal surface, $0° \leq \theta \leq 360°$. $Z_1$ and $Z_2$ are the height coordinates of the progressive multifocal surface from a reference plane. R is a radius of curvature of the progressive multifocal surface. p is a number of the high power segments or a number of the low power segments, and p is an integer greater than or equal to 3. q is a real number greater than or equal to 1, m and n are positive integers, $a_n$ is a real number, and s is an integer and $1 \leq s \leq p$.

In one or more embodiments, q=1.

In one or more embodiments, the progressive multifocal ophthalmic lens further includes a circular segment disposed at a center of circle of the progressive multifocal surface. The high power segments, the low power segments, the progressive power segments, and the circular segment form the progressive multifocal surface. The progressive multifocal surface further satisfies the following relationships:

when $0 < r < r_1$, and $[180°\cdot(2s-2)]/p < \theta < [180°\cdot(2s-1)]/p$, $a_n$ are 0, and $R=R_1$;

when $0 < r < r_1$, and $[180°\cdot(2s-1)]/p < \theta < (180°\cdot 2s)/p$, $a_n$ are 0, and $R=R_1$;

when $r_1 < r < r_0$, and $[180°\cdot(2s-2)]/p < \theta < [180°\cdot(2s-1)]/p$, q=1, and $R=R_2$; and when $r_1 < r < r_0$, and $[180°\cdot(2s-1)]/p < \theta < (180°\cdot 2s)/p$, q=1, and $R=R_2$, where $r_1$ is a radius of the circular segment, $r_0$ is the radius of the optical segment of the progressive multifocal surface, $R_1$ is the radius of curvature of the circular segment, $R_2$ is a radius of curvature of the high power segments or the low power segments, and $Z_1(r, \theta)$ and $Z_2(r, \theta)$ are smoothly connected to each other at $r=r_1$.

Another aspect of the present invention is to provide a progressive multifocal ophthalmic lens including at least three high power segments, at least three low power segments, and a plurality of progressive power segments. Shapes of the high power segments and the low power segments are sectors. The high power segments and the low power segments are disposed alternately along an arc direction of the progressive multifocal ophthalmic lens. Shapes of the progressive power segments are sectors. Two sides of each of the progressive power segments along the arc direction respectively connect one of the high power segments and one of the low power segments. The high power segments, the low power segments, and the progressive power segments form a progressive multifocal surface satisfying the following relationships:

when $[180°\cdot(2s-2)]/p < \theta < [180°\cdot(2s-1)]/p$, $$Z_1(r,\theta) = R - \sqrt{R^2 - r^2} - \left(\sum_{n=1}^{m} a_n \cdot r^n\right) \cdot \left[\cos\left[\pi \cdot \left(1 - \frac{p\cdot\theta}{180}\right)^q\right] + 1\right]; \text{ and}$$

when $[180°\cdot(2s-1)]/p < \theta < (180°\cdot 2s)/p$, $$Z_2(r,\theta) = R - \sqrt{R^2 - r^2} - \left(\sum_{n=1}^{m} a_n \cdot r^n\right) \cdot \left[\cos\left[\pi \cdot \left(\frac{p\cdot\theta}{180} - 1\right)^q\right] + 1\right],$$

where r is a radial coordinate of the progressive multifocal surface, $\theta \leq r \leq r_0$. $r_0$ is a radius of an optical segment of the progressive multifocal surface. $\theta$ is an angular coordinate of the progressive multifocal surface, $0°\leq\theta\leq360°$. $Z_1$ and $Z_2$ are height coordinates of the progressive multifocal surface from a reference plane. R is a radius of curvature of the progressive multifocal surface. p is the number of the high power segments or the number of the low power segments, and p is an integer greater than or equal to 3. q is a real number greater than or equal to 1, m and n are positive integers, $a_n$ is a real number, and s is an integer and $1\leq s\leq p$.

In one or more embodiments, $q=1$.

In one or more embodiments, the progressive multifocal ophthalmic lens further includes a circular segment disposed at a center of circle of the progressive multifocal surface. The high power segments, the low power segments, the progressive power segments, and the circular segment form the progressive multifocal surface. The progressive multifocal surface further satisfies the following relationships:

when $0<r<r_1$, and $[180°\cdot(2s-2)]/p<\theta<[180°\cdot(2s-1)]/p$, $a_n$ are 0, and $R=R_1$;

when $0<r<r_1$, and $[180°\cdot(2s-1)]/p<\theta<(180°\cdot2s)/p$, $a_n$ are 0, and $R=R_1$;

when $r_1<r<r_0$, and $[180°\cdot(2s-2)]/p<\theta<[180°\cdot(2s-1)]/p$, $q=1$, and $R=R_2$; and when $r_1<r<r_0$, and $[180°\cdot(2s-1)]/p<\theta<(180°\cdot2s)/p$, $q=1$, and $R=R_2$, where $r_1$ is a radius of the circular segment, $r_0$ is the radius of the optical segment of the progressive multifocal surface, $R_1$ is a radius of curvature of the circular segment, $R_2$ is a radius of curvature of the high power segments or the low power segments, and $Z_1(r, \theta)$ and $Z_2(r, \theta)$ are smoothly connected to each other at $r=r_1$.

Yet another aspect of the present invention is to provide a progressive multifocal ophthalmic lens including a progressive multifocal surface and a toric surface. The progressive multifocal ophthalmic lens further includes at least three high power segments, at least three low power segments, and a plurality of progressive power segments. Shapes of the high power segments and the low power segments are sectors. The high power segments and the low power segments are disposed alternately along an arc direction of the progressive multifocal ophthalmic lens. Shapes of the progressive power segments are sectors. Two sides of each of the progressive power segments along the arc direction respectively connect one of the high power segments and one of the low power segments. The high power segments, the low power segments, and the progressive power segments form the progressive multifocal surface.

In one or more embodiments, the progressive multifocal surface and the toric surface form a compound curved surface disposed at a main surface of the progressive multifocal ophthalmic lens, and the other main surface is a spherical surface or an aspherical surface.

In one or more embodiments, the progressive multifocal surface and the toric surface are respectively disposed at two main surfaces of the progressive multifocal ophthalmic lens.

The progressive multifocal ophthalmic lenses mentioned above are simultaneous visual lenses. That is, images with different focuses can be simultaneously projected onto the retina through the high power segments, the low power segments, and the progressive power segments. The human vision system or the brain selects clear images while excluding blurred images to achieve a zooming effect.

DETAILED DESCRIPTION

Figure 1:
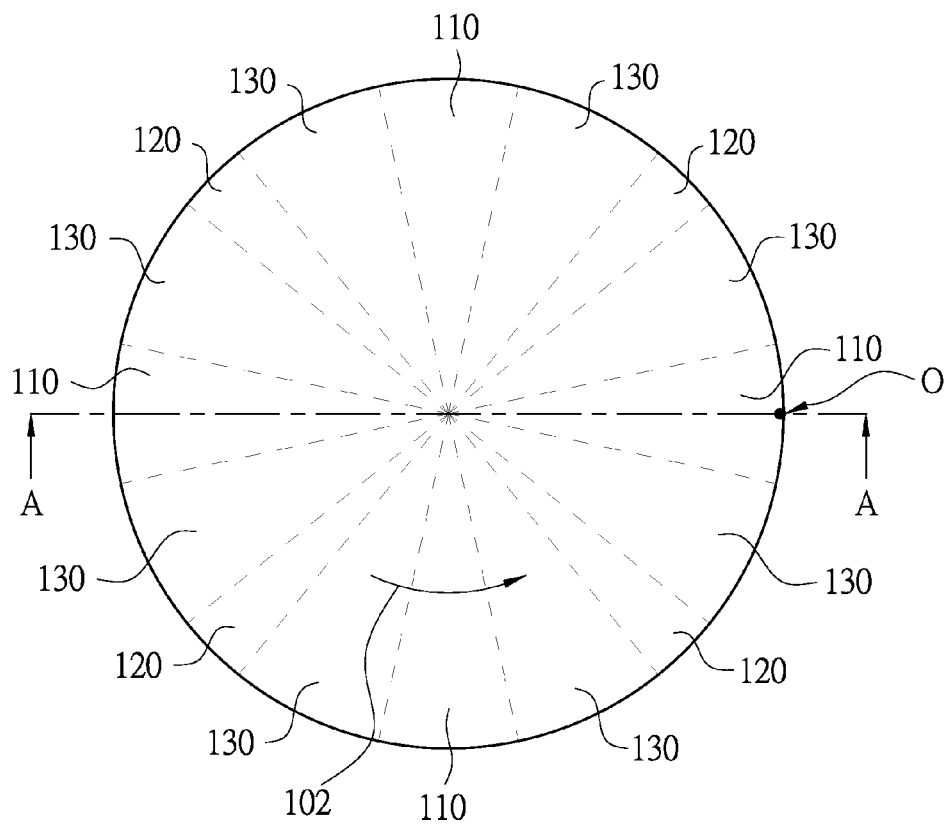
FIG. 1 is a schematic diagram of a progressive multifocal ophthalmic lens according to a first embodiment of the present invention.

Reference will now be made in detail to the present embodiments of the invention, examples of which are illustrated in the accompanying drawings. Wherever possible, the same reference numbers are used in the drawings and the description to refer to the same or like parts.

First Aspect

FIG. 1 is a schematic diagram of a progressive multifocal ophthalmic lens according to a first embodiment of the present invention. The progressive multifocal ophthalmic lens includes at least three high power segments 110, at least three low power segments 120, and a plurality of progressive power segments 130. Shapes of the high power segments 110, the low power segments 120, and the progressive power segments 130 are sectors. The high power segments 110 and the low power segments 120 are disposed alternately along an arc direction 102 of the progressive multifocal ophthalmic lens. Two sides of each of the progressive power segments 130 along the arc direction 102 respectively connect one of the high power segments 110 and one of the low power segments 120. The progressive multifocal ophthalmic lens of the present embodiment is a simultaneous visual lens. That is, images with different focuses can be simultaneously projected onto the retina through the high power segments 110, the low power segments 120, and the progressive power segments 130. The human vision system or the brain selects clear images while excludes blurred images to achieve zooming effect. The progressive multifocal ophthalmic lens mentioned above can be a contact lens or an intraocular lens, and the claimed scope is not limited in this respect.

In greater detail, all of the high power segments 110, the low power segments 120, and the progressive power segments 130 are disposed at the same main surface of the progressive multifocal ophthalmic lens to form a progressive multifocal surface, and the other main surface is a spherical surface or an aspherical surface. The progressive multifocal surface satisfies the following relationships:

when $[180° \cdot (2s-2)]/p < \theta < [180° \cdot (2s-1)]/p$, $$Z_1(r, \theta) = R - \sqrt{R^2 - r^2} + \left(\sum_{n=1}^{m} a_n \cdot r^n\right) \cdot \left[\cos\left[\pi \cdot \left(\frac{p \cdot \theta}{180}\right)^q\right] - 1\right]; \text{ and}$$

when $[180° \cdot (2s-1)]/p < \theta < (180° \cdot 2s)/p$, $$Z_2(r, \theta) = R - \sqrt{R^2 - r^2} + \left(\sum_{n=1}^{m} a_n \cdot r^n\right) \cdot \left[\cos\left[\pi \cdot \left(2 - \frac{p \cdot \theta}{180}\right)^q\right] - 1\right],$$

The aforementioned equations are represented by cylindrical coordinate. That is, r is a radial coordinate of the progressive multifocal surface, and θ is an angular coordinate of the progressive multifocal surface. With different radial coordinates r and angular coordinates θ, height coordinates $Z_1$ and $Z_2$ of different positions of the progressive multifocal surface from a reference plane can be obtained from the aforementioned equations, where $Z_1(0, \theta)$ and $Z_2(0, \theta)$ are height coordinates of the circle center or the peak of the progressive multifocal surface. In addition, $0 \leq r \leq r_0$, where $r_0$ is a radius of an optical segment of the progressive multifocal surface. $0° \leq \theta \leq 360°$. R is the radius of curvature of the progressive multifocal surface; p is a number of the high power segments and a number of the low power segments, and p is an integer greater than or equal to 3; q is a real number greater than or equal to 1; m and n are positive integers; $a_n$ is a real number, where the values of m, n, and $a_n$ can be determined by calculating from the different power segments; and s is an integer and $1 \leq s \leq p$.

In actual situations, the value of q can be determined by examining the patient. This design improves vision quality, and/or enhances light intensity of clear images.

Figure 2A:
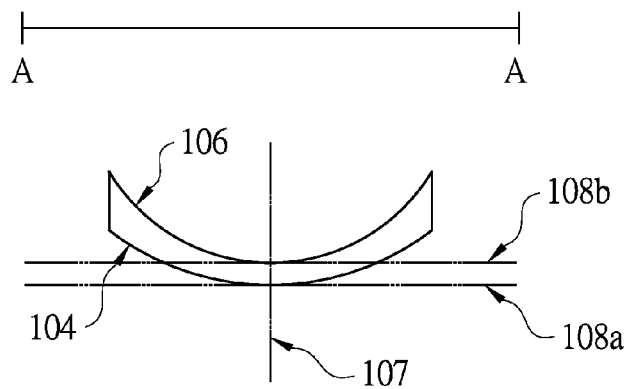
FIG. 2A is a cross-sectional view taken along line A-A of FIG. 1 according to one embodiment.

The following paragraphs provide detailed explanations with respect to the height coordinates $Z_1$ and $Z_2$. FIG. 2A is a cross-sectional view taken along line A-A of FIG. 1 according to one embodiment. In greater detail, the progressive multifocal ophthalmic lens has two main surfaces 104 and 106 opposite to each other. The main surface 106 can contact the cornea if the progressive multifocal ophthalmic lens is a contact lens. The progressive multifocal ophthalmic lens further has an optical axis 107. The main surface 104 intersects the optical axis 107 at a point, and reference plane 108a passes through the point and is tangent to the arc of main surface 104. If the progressive multifocal surface is disposed on the main surface 104, the height coordinates $Z_1$ and $Z_2$ are the height from the reference plane 108a to the progressive multifocal surface, and the main surface 106 can be a spherical surface or an aspherical surface. Similarly, the main surface 106 intersects the optical axis 107 at another point, and a reference plane 108b passes through the point and is tangent to the arc of main surface 106. If the progressive multifocal surface is disposed on the main surface 106, the height coordinates $Z_1$ and $Z_2$ are heights from the reference plane 108b to the progressive multifocal surface, and the main surface 104 can be a spherical surface or an aspherical surface.

Figure 2B:
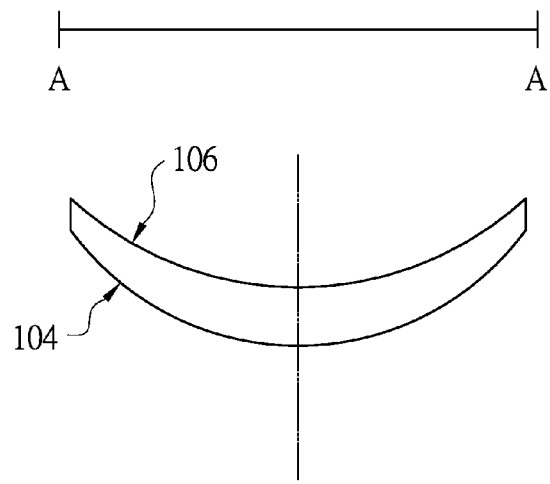
FIG. 2B is a cross-sectional view taken along line A-A of FIG. 1 according to another embodiment.

It is noted that even though the progressive multifocal ophthalmic lens of FIG. 2A is a concave lens, the claimed scope is not limited in this respect. FIG. 2B is a cross-sectional view taken along line A-A of FIG. 1 according to another embodiment. In this embodiment, the progressive multifocal ophthalmic lens is a convex lens. The power of the progressive multifocal ophthalmic lens can be determined by the radius of curvature of the main surfaces 104 and 106 and also the material and thickness of the progressive multifocal ophthalmic lens.

Reference is made again to FIG. 1. As there is a variation in height of the progressive multifocal surface, the aforementioned equations define the high power segments 110, low power segments 120, and the progressive power segments 130 therebetween. There can be no boundaries between the adjacent progressive power segment 130 and the high power segment 110, and between the adjacent progressive power segment 130 and the low power segment 120.

The progressive multifocal ophthalmic lens of the present embodiment can be used to correct a patient with presbyopia or astigmatism. For presbyopia correction, the high power segments 110 can be distance-visual segments, the low power segments 120 can be near-visual segments, and the progressive power segments 130 are configured to buffer the power variations between the high power segments 110 and the low power segments 120. Table 1 is power values of the progressive multifocal ophthalmic lens of FIG. 1 according to two examples, and the unit of the power is D (diopter). The power values of Set A can be applied to correct myopia presbyopia, and the power values of Set B can be applied to correct hyperopia presbyopia. In one or more examples, $\Delta d_1 = \Delta d_2 = +0.1$ D, and the claimed scope is not limited in this respect.

TABLE 1

The power values of the high power segments 110, the low power segments 120, and the progressive power segments 130

| | Set A | Set B |
|---|---|---|
| High power segments 110 | −5.0 D~−5.0 D + $\Delta d_1$ | +2.0 D~+2.0 D + $\Delta d_1$ |
| Low power segments 120 | −4.0 D~−4.0 D − $\Delta d_2$ | +3.0 D~+3.0 D − $\Delta d_2$ |
| Progressive power segments 130 | −5.0 D + $\Delta d_1$~−4.0 D − $\Delta d_2$ | +2.0 D + $\Delta d_1$~+3.0 D − $\Delta d_2$ |

Figure 3:
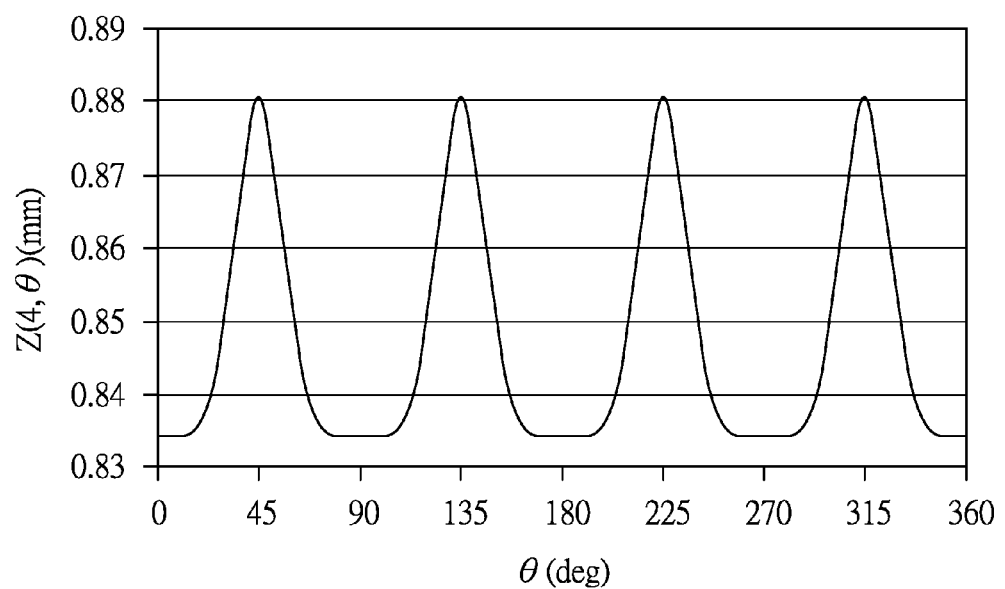
FIG. 3 is a graph of height coordinate Z from point O of FIG. 1 along the arc direction according to one example.

FIG. 3 is a graph of height coordinate Z from point O of FIG. 1 along the arc direction 102 according to one example, and Table 2 is an equation parameter table that forms the height coordinate Z of FIG. 3, where the radial coordinate r of point O is 4 mm. When $0° < \theta < 45°$, $90° < \theta < 135°$, $180° < \theta \leq 225°$, and $270° < \theta < 315°$, the height coordinate $Z=Z_1$; when $45°<\theta<90°$, $135°<\theta<180°$, $225°<\theta<270°$, and $315°<\theta<360°$, the height coordinate $Z=Z_2$. As shown in FIG. 3, the height coordinate Z varies as there is an increase of the angular coordinate θ. Reference is made to FIGS. 1 and 3. Different height coordinates Z correspond to different segments. For example, areas around the height coordinates Z of about 0.835 mm correspond to the high power segments 110, areas around the height coordinate Z of about 0.880 mm correspond to the low power segments 120, and areas around the height coordinates Z of between 0.835 mm and 0.880 mm correspond to the progressive power segments 130.

TABLE 2

The equation parameters that forms
the height coordinate Z of FIG. 3

| r | 0~4 mm | R | 10 mm | m | 3 |
|---|---|---|---|---|---|
| $r_0$ | 4 mm | p | 4 | $a_1$ | −1.0e−4 |
| θ | 0°~360° | q | 2 | $a_2$ | −2.0e−4 |
|  |  |  |  | $a_3$ | −3.0e−4 |

Reference is made again to FIG. 1. In this embodiment, the patient can use the high power segments 110, the low power segments 120, and the progressive segments 130 uniformly even though the progressive multifocal ophthalmic lens rotates, in such a way that the stabilization design of the progressive multifocal ophthalmic lens can be omitted, and the progressive multifocal ophthalmic lens is no longer low-oxygen-permeable, low comfort, and no longer requires an axis check or adjustment. Moreover, although the size of the pupil changes with the ambient light intensity, contrast, or age of the patient, with regard to the progressive multifocal ophthalmic lens of the present embodiment, the areas that the pupil respectively overlaps the high power segments 110, the low power segments 120, and the progressive power segments 130 are increased or decreased at the same ratio. For a patient with astigmatism, the vision quality respectively provided by spherical segments and cylindrical segments can be nearly identical; for a patient with presbyopia, vision quality is not compromised or sacrificed from the dilation of the pupil or changing focus between distance-viewing and near-viewing. Furthermore, the pupil can still uses all of the high power segments 110, the low power segments 120, and the progressive segments 130 when the progressive multifocal ophthalmic lens shifts, and all of the segments are approximately symmetric with respect to the eye axis, thus vision quality is only slightly affected.

Figure 4:
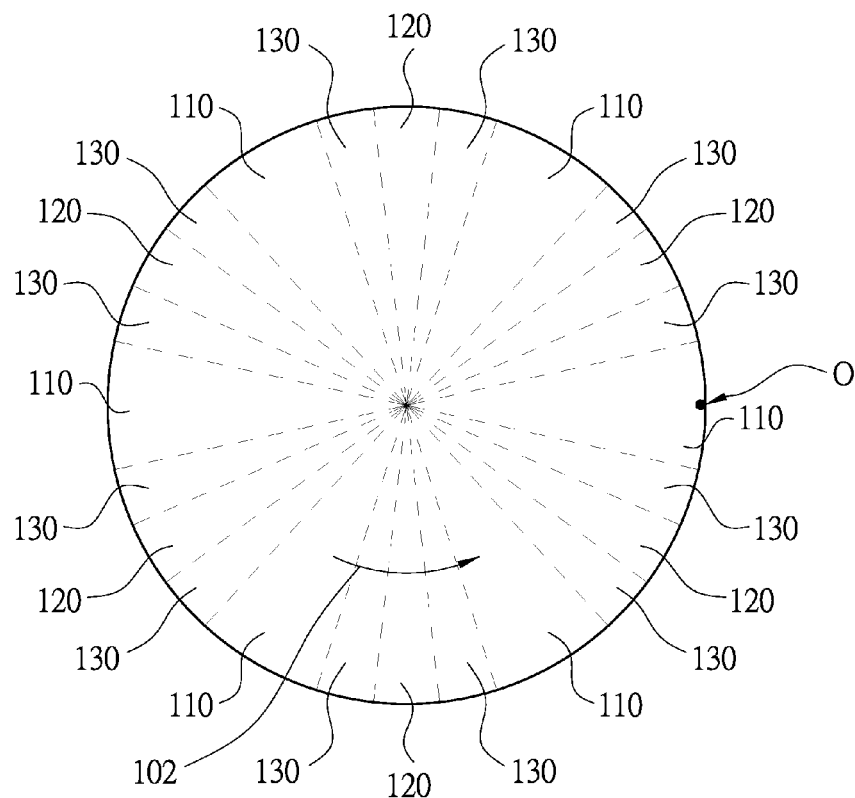
FIG. 4 is a schematic diagram of a progressive multifocal ophthalmic lens according to a second embodiment of the present invention.

FIG. 4 is a schematic diagram of a progressive multifocal ophthalmic lens according to a second embodiment of the present invention. The difference between the second embodiment and the first embodiment pertains to the value of p. In this embodiment, p=6. The progressive multifocal ophthalmic lens of the present invention can be applied to correct a patient with presbyopia or astigmatism. For astigmatism correction, the high power segments 110 are configured to correct eye ametropia, the low power segments 120 are configured to correct astigmatism, and the progressive power segments 130 disposed between the high power segments 110 and low power segments 120 are configured to buffer the power variations between the high power segments 110 and the low power segments 120. In one or more examples, the power values of the high power segments 110, the low power segments 120, and the progressive power segments 130 are shown in Table 1, and the claimed scope are not limited in this respect. The Set A can be applied to correct myopic astigmatism, and the Set B can be applied to correct hypermetropic astigmatism.

Figure 5:
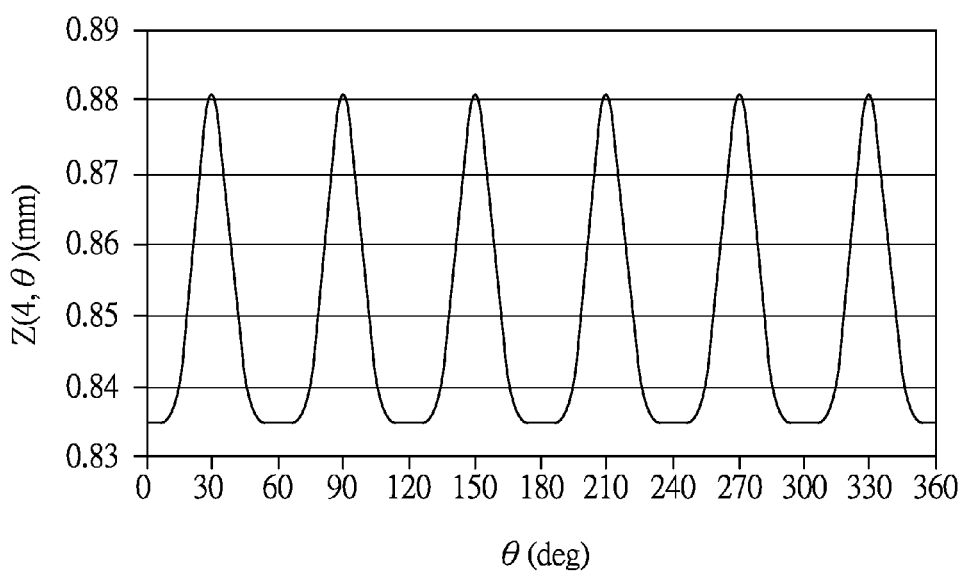
FIG. 5 is a graph of height coordinate Z from point O of FIG. 4 along the arc direction according to one example.

FIG. 5 is a graph of height coordinate Z from point O of FIG. 4 along the arc direction 102 according to one example, and Table 3 is an equation parameter table that forms the height coordinate Z of FIG. 5, where the radial coordinate r of point O is 4 mm. When $0°<\theta<30°$, $60°<\theta<90°$, . . . , $240°<\theta<270°$, and $300°<\theta<330°$, the height coordinate $Z=Z_1$; when $30°<\theta<60°$, $90°<\theta<120°$, . . . , $270°<\theta<300°$, and $330°<\theta<360°$, the height coordinate $Z=Z_2$. As shown in FIG. 5, the height coordinate Z varies as there is an increase in the angular coordinate θ. Reference is made to FIGS. 4 and 5. Different height coordinates Z correspond to different segments. For example, areas around the height coordinates Z of about 0.835 mm correspond to the high power segments 110, areas around the height coordinates Z of about 0.880 mm correspond to the low power segments 120, and areas around the height coordinates Z of between 0.835 mm and 0.880 mm correspond to the progressive power segments 130. Other features of the second embodiment are the same as those of the first embodiment, and therefore, a description in this regard will not be provided hereinafter.

TABLE 3

The equation parameters that forms
the height coordinate Z of FIG. 5

| r | 0~4 mm | R | 10 mm | m | 3 |
|---|---|---|---|---|---|
| $r_0$ | 4 mm | p | 6 | $a_1$ | −1.0e−4 |
| θ | 0°~360° | q | 2 | $a_2$ | −2.0e−4 |
|  |  |  |  | $a_3$ | −3.0e−4 |

Figure 6:
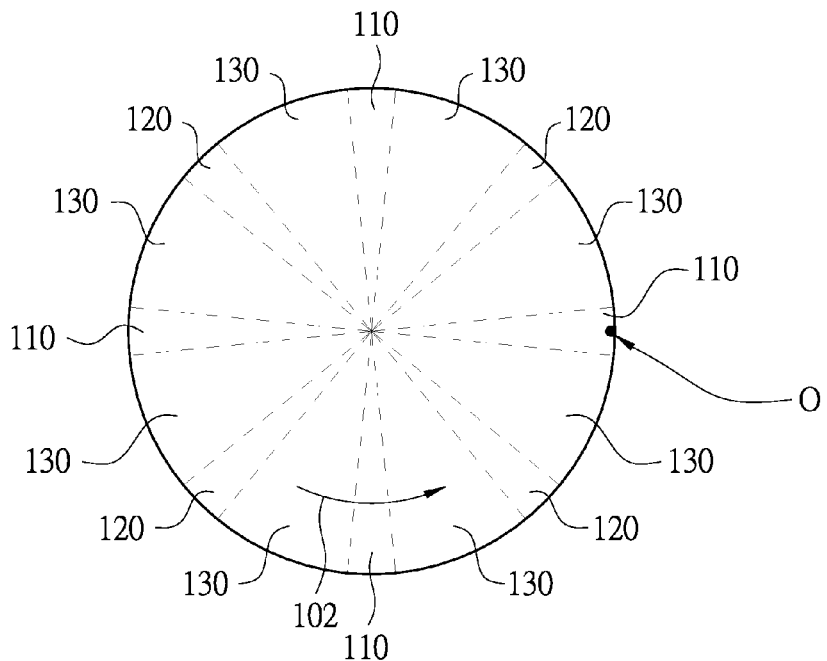
FIG. 6 is a schematic diagram of a progressive multifocal ophthalmic lens according to a third embodiment of the present invention.

FIG. 6 is a schematic diagram of a progressive multifocal ophthalmic lens according to a third embodiment of the present invention. The difference between the third embodiment and the first embodiment pertains to the value of q. In this embodiment, q=1.

Figure 7:
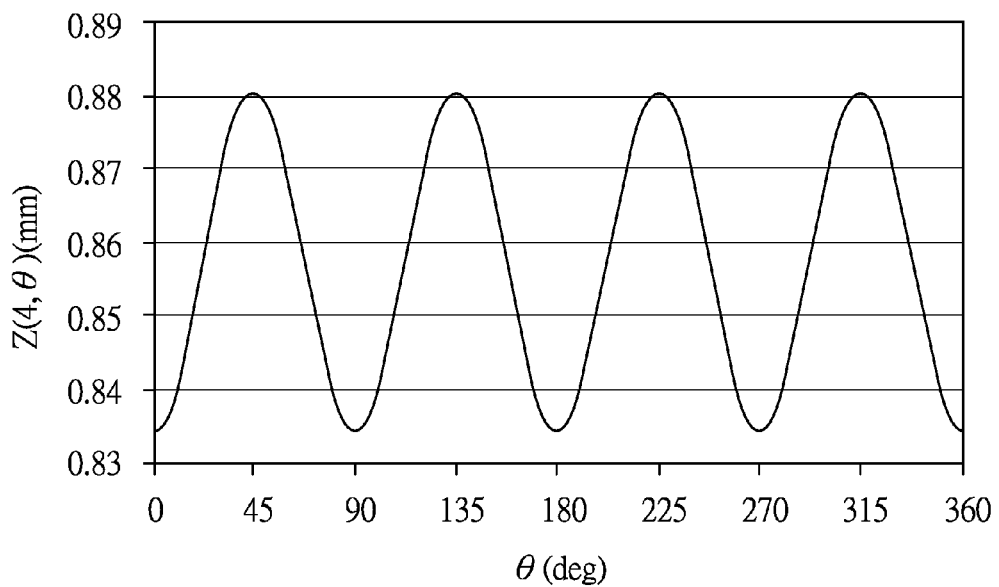
FIG. 7 is a graph of height coordinate Z from point O of FIG. 6 along the arc direction according to one example.

The progressive multifocal ophthalmic lens of the present embodiment can be applied to correct a patient with presbyopia or astigmatism, where the power values of the high power segments 110, the low power segments 120, and the progressive power segments 130 are shown in Table 1, and the claimed scope is not limited in this respect. FIG. 7 is a graph of height coordinate Z from point O of FIG. 6 along the arc direction 102 according to one example, and Table 4 is an equation parameter table that forms the height coordinate Z of FIG. 7, where the radial coordinate r of point O is 4 mm. When $0°<\theta<45°$, $90°<\theta<135°$, $180°<\theta<225°$, and $270°<\theta<315°$, the height coordinate $Z=Z_1$; when $45°<\theta<90°$, $135°<\theta<180°$, $225°<\theta<270°$, and $315°<\theta<360°$, the height coordinate $Z=Z_2$. As shown in FIG. 7, the height coordinate Z varies as there is an increase in the angular coordinate θ. Reference is made to FIGS. 6 and 7. Different height coordinates Z correspond to different segments. For example, areas around the height coordinates Z of about 0.835 mm correspond to the high power segments 110, areas around the height coordinate Z of about 0.880 mm correspond to the low power segments 120, and areas around the height coordinates Z of between 0.835 mm and 0.880 mm correspond to the progressive power segments 130. Other features of the third embodiment are the same as those of the first embodiment, and therefore, a description in this regard will not be provided hereinafter.

TABLE 4

The equation parameters that forms
the height coordinate Z of FIG. 7

| r | 0~4 mm | R | 10 mm | m | 3 |
|---|---|---|---|---|---|
| $r_0$ | 4 mm | p | 4 | $a_1$ | −1.0e−4 |
| θ | 0°~360° | q | 1 | $a_2$ | −2.0e−4 |
|  |  |  |  | $a_3$ | −3.0e−4 |

Figure 8:
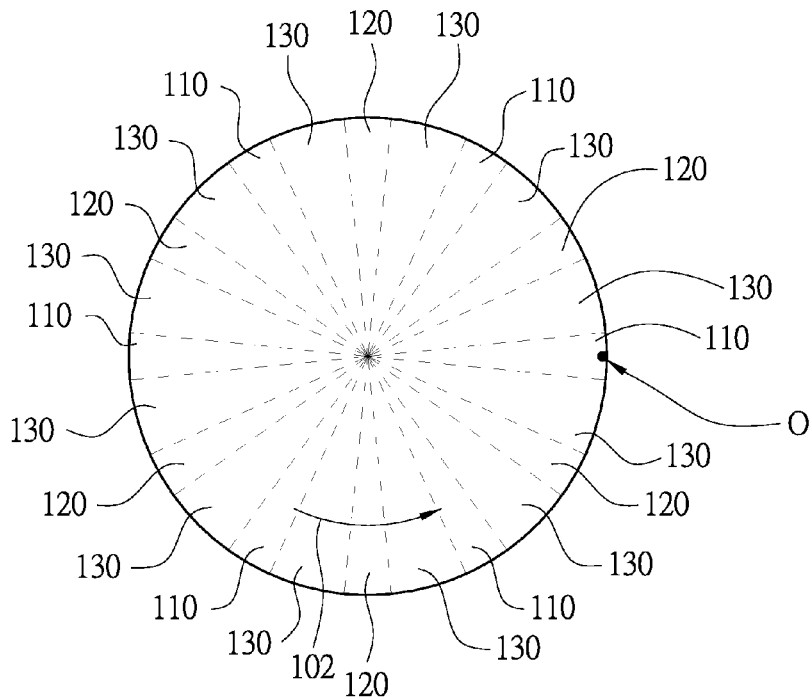
FIG. 8 is a schematic diagram of a progressive multifocal ophthalmic lens according to a fourth embodiment of the present invention.

FIG. 8 is a schematic diagram of a progressive multifocal ophthalmic lens according to a fourth embodiment of the present invention. The difference between the fourth embodiment and the second embodiment pertains to the value of q. In this embodiment, q=1.

Figure 9:
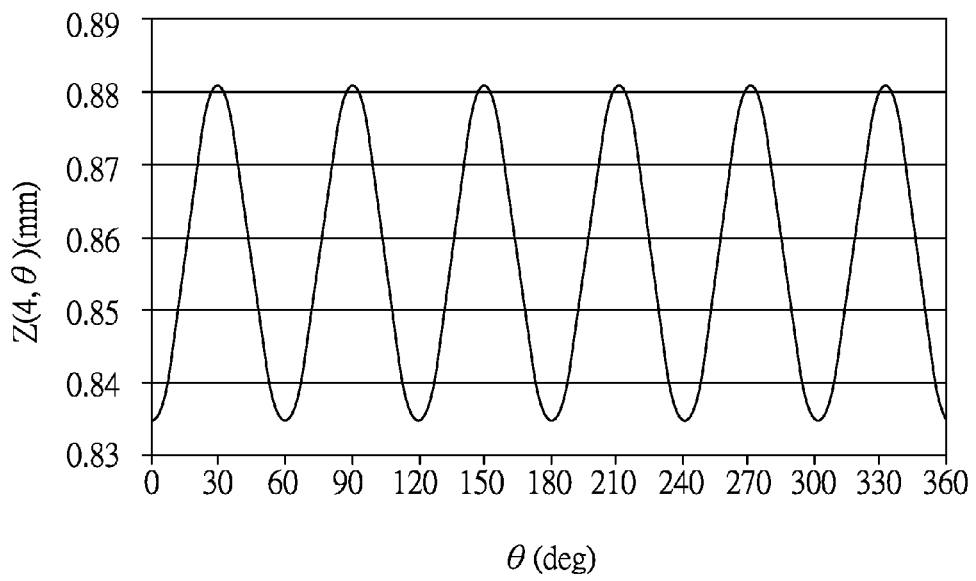
FIG. 9 is a graph of height coordinate Z from point O of FIG. 8 along the arc direction according to one example.

The progressive multifocal ophthalmic lens of the present invention can be applied to correct a patient with presbyopia or astigmatism, where the power values of the high power segments 110, the low power segments 120, and the progressive power segments 130 are shown in Table 1, and the claimed scope is not limited in this respect. FIG. 9 is a graph of height coordinate Z from point O of FIG. 8 along the arc direction 102 according to one example, and Table 5 is an equation parameter table that forms the height coordinate Z of FIG. 9, where the radial coordinate r of point O is 4 mm. When $0°<\theta<30°, 60°<\theta<90°, \ldots, 240°<\theta<270°$, and $300°<\theta<330°$, the height coordinate $Z=Z_1$; when $30°<\theta<60°, 90°<\theta<120°, \ldots, 270°<\theta<300°$, and $330°<\theta<360°$, the height coordinate $Z=Z_2$. As shown in FIG. 9, the height coordinate Z varies as there is an increase in the angular coordinate $\theta$. Reference is made to FIGS. 8 and 9. Different height coordinates Z correspond to different segments. For example, areas around the height coordinates Z of about 0.835 mm correspond to the high power segments 110, areas around the height coordinate Z of about 0.880 mm correspond to the low power segments 120, and areas around the height coordinates Z of between 0.835 mm and 0.880 mm correspond to the progressive power segments 130. Other features of the fourth embodiment are the same as those of the second embodiment, and therefore, a description in this regard will not be provided hereinafter.

TABLE 5

The equation parameters that forms the height coordinate Z of FIG. 9

| r | 0~4 mm | R | 10 mm | m | 3 |
|---|---|---|---|---|---|
| $r_0$ | 4 mm | p | 6 | $a_1$ | $-1.0e-4$ |
| $\theta$ | 0°~360° | q | 1 | $a_2$ | $-2.0e-4$ |
| | | | | $a_3$ | $-3.0e-4$ |

Figure 10:
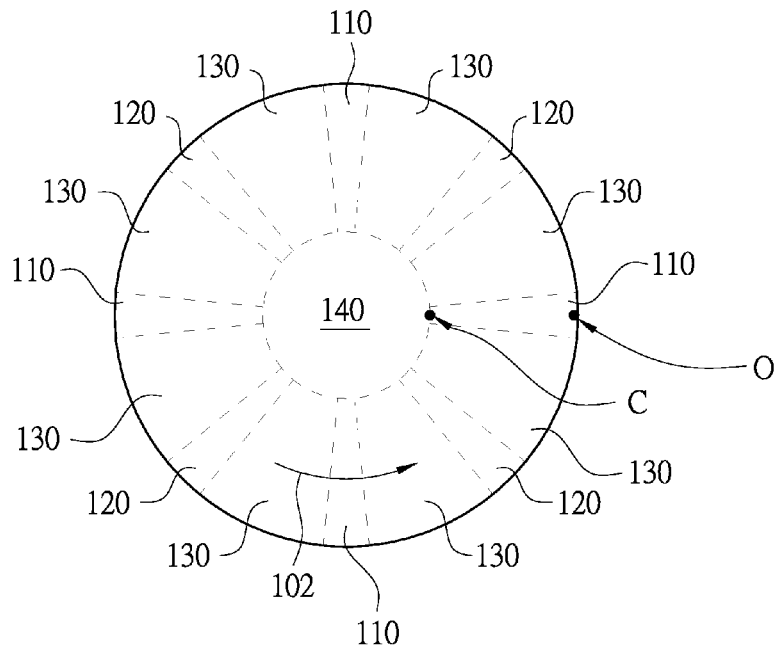
FIG. 10 is a schematic diagram of a progressive multifocal ophthalmic lens according to a fifth embodiment of the present invention.

FIG. 10 is a schematic diagram of a progressive multifocal ophthalmic lens according to a fifth embodiment of the present invention. The difference between the fifth embodiment and the third embodiment pertains to the presence of a circular segment 140. In this embodiment, the progressive multifocal ophthalmic lens further includes the circular segment 140 disposed at a center of circle of the progressive multifocal surface. The high power segments 110, the low power segments 120, the progressive power segments 130, and the circular segment 140 form the progressive multifocal surface.

In greater detail, the progressive multifocal surface not only satisfies the following relationships (as mentioned in the first embodiment):

when $[180° \cdot (2s-2)]/p < \theta < [180° \cdot (2s-1)]/p$, $$Z_1(r, \theta) = R - \sqrt{R^2 - r^2} + \left(\sum_{n=1}^{m} a_n \cdot r^n\right) \cdot \left[\cos\left[\pi \cdot \left(\frac{p \cdot \theta}{180}\right)^q\right] - 1\right]; \text{ and}$$

when $[180° \cdot (2s-1)]/p < \theta < (180° \cdot 2s)/p$, $$Z_2(r, \theta) = R - \sqrt{R^2 - r^2} + \left(\sum_{n=1}^{m} a_n \cdot r^n\right) \cdot \left[\cos\left[\pi \cdot \left(2 - \frac{p \cdot \theta}{180}\right)^q\right] - 1\right],$$

but also satisfies the following relationships:

when $0<r<r_1$, and $[180° \cdot (2s-2)]/p<\theta<[180° \cdot (2s-1)]/p$, $a_n$ are 0, and $R=R_1$;

when $0<r<r_1$, and $[180° \cdot (2s-1)]/p<\theta<(180° \cdot 2s)/p$, $a_n$ are 0, and $R=R_1$;

when $r_1<r<r_0$, and $[180° \cdot (2s-2)]/p<\theta<[180° \cdot (2s-1)]/p$, $q=1$, and $R=R_2$; and when $r_1<r<r_0$, and $[180° \cdot (2s-1)]/p<\theta<(180° \cdot 2s)/p$, $q=1$, and $R=R_2$, where $r_1$ is a radius of the circular segment 140, $r_0$ is the radius of the optical segment of the progressive multifocal surface. $R_1$ is a radius of curvature of the circular segment 140, $R_2$ is a radius of curvature of the high power segments 110 or the low power segments 120, and $Z_1(r, \theta)$ and $Z_2(r, \theta)$ are smoothly connected to each other at $r=r_1$, where is the adjacent positions between the circular segment 140 and each of the high power segments 110, the low power segments 120, and the progressive power segments 130.

It is noted that the power of the circular segment 140 can be the same as that of the high power segments 110 or low power segments 120, i.e., $R_1=R_2$, or the power of the circular segment 140 can be different from that of the high power segments 110 or the low power segments 120, i.e., $R_1 \neq R_2$.

Figure 11:
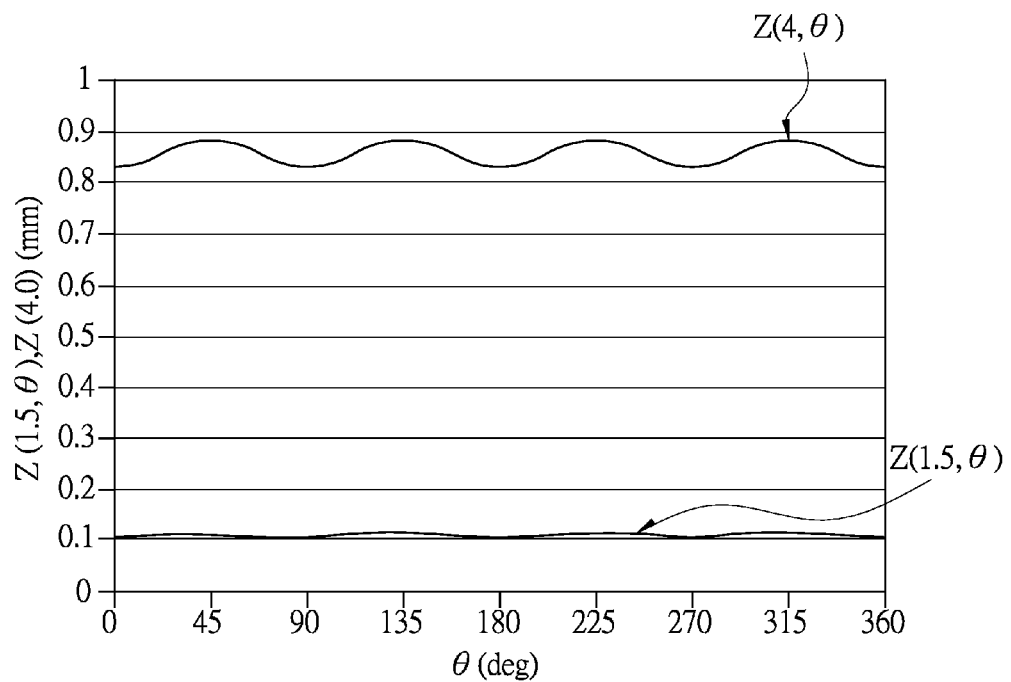
FIG. 11 is a graph of height coordinate Z respectively from point O and point C of FIG. 10 along the arc direction according to one example.

The progressive multifocal ophthalmic lens of the present invention can be applied to correct a patient with presbyopia, where the power values of the high power segments 110, the low power segments 120, and the progressive power segments 130 are shown in Table 1, the power value of the circular segment 140 can be the same as that of the high power segment 110, and the claimed scope is not limited in this respect. FIG. 11 is a graph of height coordinates Z respectively from point O and point C of FIG. 10 along the arc direction 102 according to one example, and Table 6 is an equation parameter table that forms the height coordinate Z of FIG. 11, where the radial coordinate r of point O is 4 mm, and the radial coordinate r of point C is 1.5 mm. When $0°<\theta<45°, 90°<\theta<135°, 180°<\theta<225°$, and $270°<\theta<315°$, the height coordinate $Z=Z_1$; when $45°<\theta<90°, 135°<\theta<180°, 225°<\theta<270°$, and $315°<\theta<360°$, the height coordinate $Z=Z_2$. When r<1.5 mm, the height coordinate Z is approximately constant as increase of the angular coordinate $\theta$, and as shown in FIG. 11, when r≥1.5 mm, the height coordinate Z varies as there is an increase in the angular coordinate $\theta$. Reference is made to FIGS. 10 and 11. When r<1.5 mm, the height coordinates Z correspond to the circular segment 140, and when r≥1.5 mm, different height coordinates Z correspond to different segments. For example, areas around the height coordinates Z of about 0.835 mm correspond to the high power segments 110, areas around the height coordinate Z of about 0.880 mm correspond to the low power segments 120, and areas around the height coordinates Z of between 0.835 mm and 0.880 mm correspond to the progressive power segments 130.

TABLE 6

The equation parameters that forms the height coordinate Z of FIG. 11

| r | 0~4 mm | $R_1$ | 10 mm | m | 3 |
|---|---|---|---|---|---|
| $r_1$ | 1.5 mm | $R_2$ | 10 mm | $a_1$ | $-1.0e-4$ |
| $r_0$ | 4 mm | p | 4 | $a_2$ | $-2.0e-4$ |
| $\theta$ | 0°~360° | q | 1 | $a_3$ | $-3.0e-4$ |

It is noted that even though the progressive multifocal ophthalmic lens of the present invention is used to correct presbyopia, the progressive multifocal ophthalmic lens can be used to correct astigmatism according to actual requirements. Other features of the fifth embodiment are the same as those of the third embodiment, and therefore, a description in this regard will not be provided hereinafter.

It is noted that the values of p(=4 or 6) in the aforementioned embodiments are illustrative only and should not limit the scope of the claimed invention. A person having ordinary skill in the art may select a suitable value of p according to actual requirements.

Second Aspect

Figure 12:
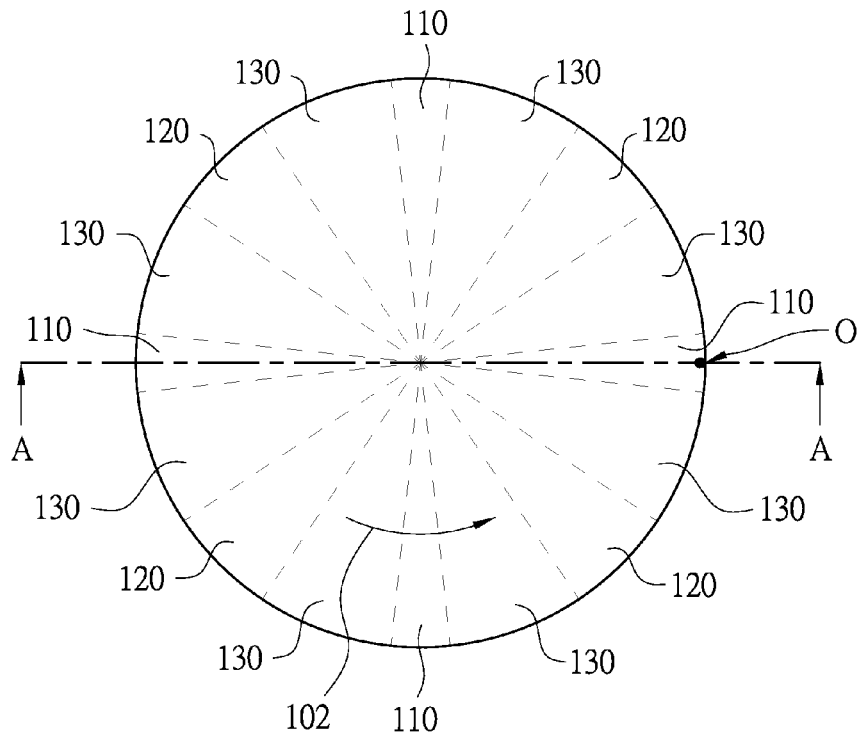
FIG. 12 is a schematic diagram of a progressive multifocal ophthalmic lens according to a sixth embodiment of the present invention.

FIG. 12 is a schematic diagram of a progressive multifocal ophthalmic lens according to a sixth embodiment of the present invention. The progressive multifocal ophthalmic lens includes at least three high power segments 110, at least three low power segments 120, and a plurality of progressive power segments 130. Shapes of the high power segments 110, the low power segments 120, and the progressive power segments 130 are sectors. The high power segments 110 and the low power segments 120 are disposed alternately along an arc direction 102 of the progressive multifocal ophthalmic lens. Two sides of each of the progressive power segments 130 along the arc direction 102 respectively connect one of the high power segments 110 and one of the low power segments 120. The progressive multifocal ophthalmic lens of the present embodiment is a simultaneous visual lens, that is, images with different focuses can be simultaneously projected onto the retina through the high power segments 110, the low power segments 120, and the progressive power segments 130. The human vision system or the brain selects clear images while excluding blurred images to achieve a zooming effect. The progressive multifocal ophthalmic lens mentioned above can be a contact lens or an intraocular lens, and the claimed scope is not limited in this respect.

In greater detail, all of the high power segments 110, the low power segments 120, and the progressive power segments 130 are disposed at the same main surface of the progressive multifocal ophthalmic lens to form a progressive multifocal surface, and the other main surface is a spherical surface or an aspherical surface. The progressive multifocal surface satisfies the following relationships:

when $[180° \cdot (2s-2)]/p < \theta < [180° \cdot (2s-1)]/p$, $$Z_1(r, \theta) = R - \sqrt{R^2 - r^2} - \left(\sum_{n=1}^{m} a_n \cdot r^n\right) \cdot \left[\cos\left[\pi \cdot \left(1 - \frac{p \cdot \theta}{180}\right)^q\right] + 1\right]; \text{ and}$$

when $[180° \cdot (2s-1)]/p < \theta < (180° \cdot 2s)/p$, $$Z_2(r, \theta) = R - \sqrt{R^2 - r^2} - \left(\sum_{n=1}^{m} a_n \cdot r^n\right) \cdot \left[\cos\left[\pi \cdot \left(\frac{p \cdot \theta}{180} - 1\right)^q\right] + 1\right].$$

The aforementioned equations are represented by cylindrical coordinate. That is, r is a radial coordinate of the progressive multifocal surface, and $\theta$ is an angular coordinate of the progressive multifocal surface. With different radial coordinates r and angular coordinates $\theta$, height coordinates $Z_1$ and $Z_2$ of different positions of the progressive multifocal surface from a reference plane can be obtained from the aforementioned equations. $Z_1(0, \theta)$ and $Z_2(0, \theta)$ are height coordinates of the circle center or the peak of the progressive multifocal surface. In addition, $0 \leq r \leq r_0$, where $r_0$ is a radius of an optical segment of the progressive multifocal surface. $0° \leq \theta \leq 360°$. R is a radius of curvature of the progressive multifocal surface; p is a number of the high power segments 110 and a number of the low power segments 120, and p is an integer greater than or equal to 3; q is a real number greater than or equal to 1; m and n are positive integers; $a_n$ is a real number, the values of m, n, and $a_n$ can be determined by calculating using different powers; and s is an integer and $1 \leq s \leq p$.

In actual situations, the value of q can be determined by the diopter of a patient. This design improves vision quality, or enhances light intensity of the clear images.

The following paragraphs provide detailed explanations with respect to the height coordinates $Z_1$ and $Z_2$. In greater detail, the cross-sectional view taken along line A-A of FIG. 12 can be the same as the cross-sectional view taken along line A-A of FIG. 1, that is, the cross-sectional view of FIG. 12 can be represented by FIG. 2A or 2B. Other cross-sectional features of the sixth embodiment are the same as those of the embodiments of FIGS. 2A and 2B, and therefore, a description in this regard will not be provided hereinafter.

As the height variation of the progressive multifocal surface, the aforementioned equations define the high power segments 110, low power segments 120, and the progressive power segments 130 therebetween. There can be no boundaries between the adjacent progressive power segment 130 and the high power segment 110, and between the adjacent progressive power segment 130 and the low power segment 120.

The progressive multifocal ophthalmic lens of the present embodiment can be used to correct a patient with presbyopia or astigmatism. For presbyopia correction, the high power segments 110 can be distance-visual segments, the low power segments 120 can be near-visual segments, and the progressive power segments 130 are configured to buffer the power variations between the high power segments 110 and the low power segments 120.

Table 7 is power values of the progressive multifocal ophthalmic lens of FIG. 12 according to two examples, and the unit of the power is D (diopter). The power values of Set A can be applied to correct myopic presbyopia, and the power values of Set B can be applied to correct hypermetropic presbyopia. In one or more examples, $\Delta d_1 = \Delta d_2 = +0.1$ D, and the claimed scope is not limited in this respect.

TABLE 7

The power values of the high power segments 110, the low power segments 120, and the progressive power segments 130

|  | Set A | Set B |
|---|---|---|
| High power segments 110 | −5.0 D~−5.0 D + $\Delta d_1$ | +2.0 D~+2.0 D + $\Delta d_1$ |
| Low power segments 120 | −4.0 D~−4.0 D − $\Delta d_2$ | +3.0 D~+3.0 D − $\Delta d_2$ |
| Progressive power segments 130 | −5.0 D + $\Delta d_1$~−4.0 D − $\Delta d_2$ | +2.0 D + $\Delta d_1$~+3.0 D − $\Delta d_2$ |

Figure 13:
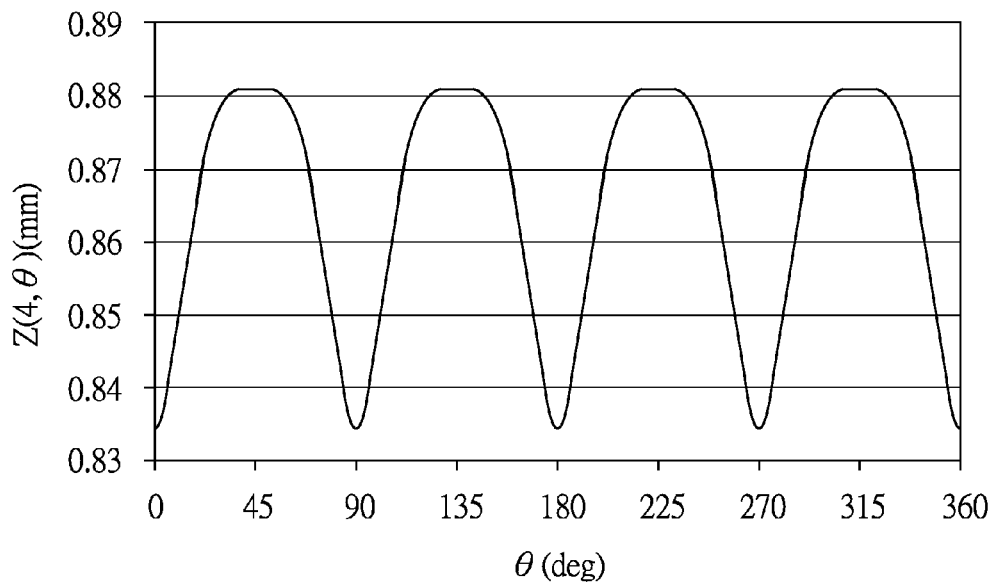
FIG. 13 is a graph of height coordinate Z from point O of FIG. 12 along the arc direction according to one example.

FIG. 13 is a graph of height coordinate Z from point O of FIG. 12 along the arc direction 102 according to one example, and Table 8 is an equation parameter table that forms the height coordinate Z of FIG. 13, where the radial coordinate r of point O is 4 mm. When $0° < \theta < 45°$, $90° < \theta < 135°$, $180° < \theta < 225°$, and $270° < \theta < 315°$, the height coordinate $Z = Z_1$; when $45° < \theta < 90°$, $135° < \theta < 180°$, $225° < \theta < 270°$, and $315° < \theta < 360°$, the height coordinate $Z = Z_2$. As shown in FIG. 13, the height coordinate Z varies as there is an increase in the angular coordinate $\theta$. Reference is made to FIGS. 12 and 13. Different height coordinates Z correspond to different segments. For example, areas around the height coordinates Z of about 0.835 mm correspond to the high power segments 110, areas around the height coordinate Z of about 0.880 mm correspond to the low power segments 120, and areas around the height coordinates Z of between 0.835 mm and 0.880 mm correspond to the progressive power segments 130.

TABLE 8

The equation parameters that forms
the height coordinate Z of FIG. 13

| r | 0~4 mm | R | 10 mm | m | 3 |
|---|---|---|---|---|---|
| $r_0$ | 4 mm | p | 4 | $a_1$ | −1.0e−4 |
| θ | 0°~360° | q | 2 | $a_2$ | −2.0e−4 |
| | | | | $a_3$ | −3.0e−4 |

Reference is made again to FIG. 12. In this embodiment, the patient can uses the high power segments 110, the low power segments 120, and the progressive segments 130 uniformly even though the progressive multifocal ophthalmic lens rotates, such that a stabilization design of the progressive multifocal ophthalmic lens can be omitted, and the progressive multifocal ophthalmic lens is no longer low-oxygen-permeable, low comfort, and no longer requires an axis-check or adjustment. Moreover, although the size of the pupil changes with the ambient light intensity, contrast, or age of the patient, with regard to the progressive multifocal ophthalmic lens of the present embodiment, the areas that the pupil respectively overlaps the high power segments 110, the low power segments 120, and the progressive power segments 130 are increased or decreased at the same ratio. For a patient with astigmatism, the vision quality respectively provided by the spherical segments and the cylindrical segments can be nearly identical, and for a patient with presbyopia, vision quality is not compromised or sacrificed from the dilation of the pupil or changing focus between distance-viewing and near-viewing. Furthermore, the pupil can still uses all of the high power segments 110, the low power segments 120, and the progressive segments 130 when the progressive multifocal ophthalmic lens shifts, and all of the segments are approximately symmetric with respect to the eye axis, thus vision quality is only slightly affected.

Figure 14:
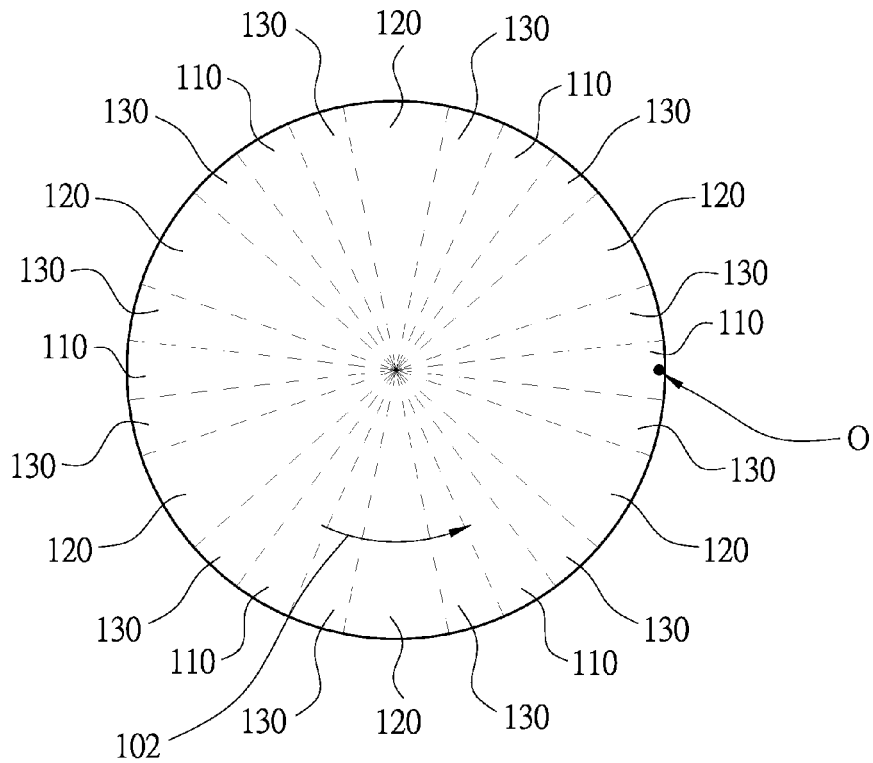
FIG. 14 is a schematic diagram of a progressive multifocal ophthalmic lens according to a seventh embodiment of the present invention.

FIG. 14 is a schematic diagram of a progressive multifocal ophthalmic lens according to a seventh embodiment of the present invention. The difference between the seventh embodiment and the sixth embodiment pertains to the value of p. In this embodiment, p=6. The progressive multifocal ophthalmic lens of the present invention can be applied to correct a patient with presbyopia or astigmatism. For astigmatism correction, the high power segments 110 are configured to correct eye ametropia, the low power segments 120 are configured to correct astigmatism, and the progressive power segments 130 disposed between the high power segments 110 and low power segments 120 are configured to buffer the power variations between the high power segments 110 and the low power segments 120. In one or more embodiments, the power values of the high power segments 110, the low power segments 120, and the progressive power segments 130 are shown in Table 7, and the claimed scope is not limited in this respect. The Set A can be applied to correct myopic astigmatism, and the Set B can be applied to correct hypermetropic astigmatism.

Figure 15:
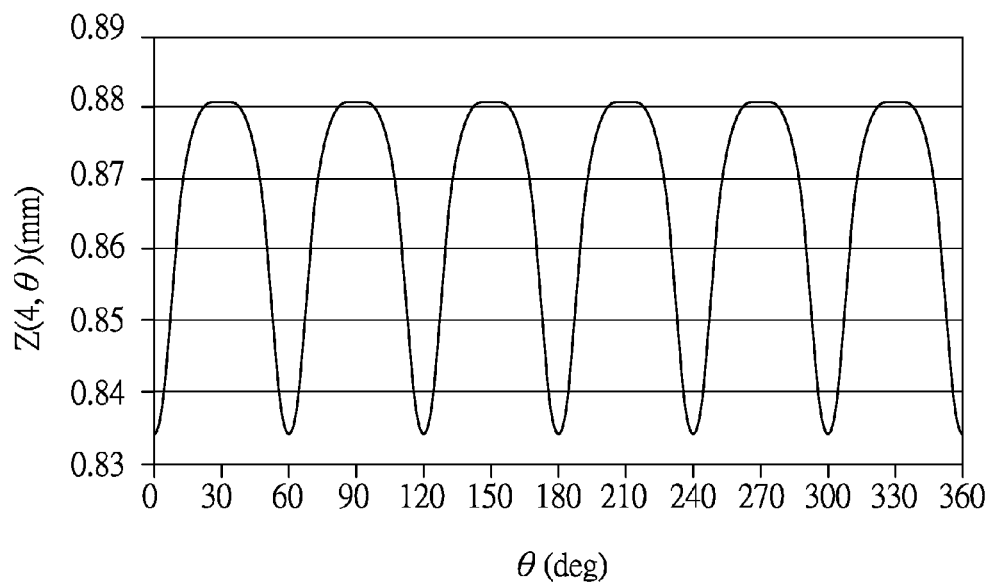
FIG. 15 is a graph of height coordinate Z from point O of FIG. 14 along the arc direction according to one example.

FIG. 15 is a graph of height coordinate Z from point O of FIG. 14 along the arc direction 102 according to one example, and Table 9 is an equation parameter table that forms the height coordinate Z of FIG. 15, where the radial coordinate r of point O is 4 mm. When 0°<θ<30°, 60°<θ<90°, . . . , 240°<θ<270°, and 300°<θ<330°, the height coordinate Z=$Z_1$; when 30°<θ<60°, 90°<θ<120°, . . . , 270°<θ<300°, and 330°<θ<360°, the height coordinate Z=$Z_2$. As shown in FIG. 15, the height coordinate Z varies as there is an increase in the angular coordinate θ. Reference is made to FIGS. 14 and 15. Different height coordinates Z correspond to different segments. For example, areas around the height coordinates Z of about 0.835 mm correspond to the high power segments 110, areas around the height coordinates Z of about 0.880 mm correspond to the low power segments 120, and areas around the height coordinates Z of between 0.835 mm and 0.880 mm correspond to the progressive power segments 130. Other features of the seventh embodiment are the same as those of the sixth embodiment, and therefore, a description in this regard will not be provided hereinafter.

TABLE 9

The equation parameters that forms
the height coordinate Z of FIG. 15

| r | 0~4 mm | R | 10 mm | m | 3 |
|---|---|---|---|---|---|
| $r_0$ | 4 mm | p | 6 | $a_1$ | −1.0e−4 |
| θ | 0°~360° | q | 2 | $a_2$ | −2.0e−4 |
| | | | | $a_3$ | −3.0e−4 |

In one or more embodiments, q=1. The schematic diagram thereof is shown in FIG. 6 or FIG. 8, and the examples of power values can be shown in Table 7. However, the claimed scope is not limited in this respect.

In one or more embodiments, the progressive multifocal ophthalmic lens can further include a circular segment 140 (see FIG. 10) disposed at a center of circle of the progressive multifocal surface. The high power segments 110, the low power segments 120, the progressive power segments 130, and the circular segment 140 (all see FIG. 10) form the progressive multifocal surface.

In greater detail, the progressive multifocal surface not only satisfies the following relationships (as mentioned in the sixth embodiment):

when $[180° \cdot (2s-2)]/p < \theta < [180° \cdot (2s-1)]/p$, $$Z_1(r, \theta) = R - \sqrt{R^2 - r^2} - \left(\sum_{n=1}^{m} a_n \cdot r^n\right) \cdot \left[\cos\left[\pi \cdot \left(1 - \frac{p \cdot \theta}{180}\right)^q\right] + 1\right]; \text{ and}$$

when $[180° \cdot (2s-1)]/p < \theta < (180° \cdot 2s)/p$, $$Z_2(r, \theta) = R - \sqrt{R^2 - r^2} - \left(\sum_{n=1}^{m} a_n \cdot r^n\right) \cdot \left[\cos\left[\pi \cdot \left(\frac{p \cdot \theta}{180} - 1\right)^q\right] + 1\right],$$

but also satisfies the following relationships:

when $0<r<r_1$, and $[180°\cdot(2s-2)]/p<\theta<[180°\cdot(2s-1)]/p$, $a_n$ are 0, and $R=R_1$;

when $0<r<r_1$, and $[180°\cdot(2s-1)]/p<\theta<(180°\cdot 2s)/p$, $a_n$ are 0, and $R=R_1$;

when $r_1<r<r_0$, and $[180°\cdot(2s-2)]/p<\theta<[180°\cdot(2s-1)]/p$, q=1, and $R=R_2$; and when $r_1<r<r_0$, and $[180°\cdot(2s-1)]/p<\theta<(180°\cdot 2s)/p$, q=1, and $R=R_2$, where $r_1$ is a radius of the circular segment 140, $r_0$ is the radius of the optical segment of the progressive multifocal surface. $R_1$ is a radius of curvature of the circular segment 140, $R_2$ is a radius of curvature of the high power segments 110 or the low power segments 120. $Z_1$ (r, θ) and $Z_2$ (r, θ) are smoothly connected to each other at r=$r_1$, where is the adjacent positions between the circular segment 140 and each of the high power segments 110, the low power segments 120, and the progressive power segments 130. Other features of the present embodiment are the same as those of the sixth embodiment, and therefore, a description in this regard will not be provided hereinafter.

It is noted that the values of p(=4 or 6) in the aforementioned embodiments are illustrative only and should not limit the scope of the claimed invention. A person having ordinary skill in the art may select a suitable value of p according to actual requirements.

Third Aspect

Figure 16:
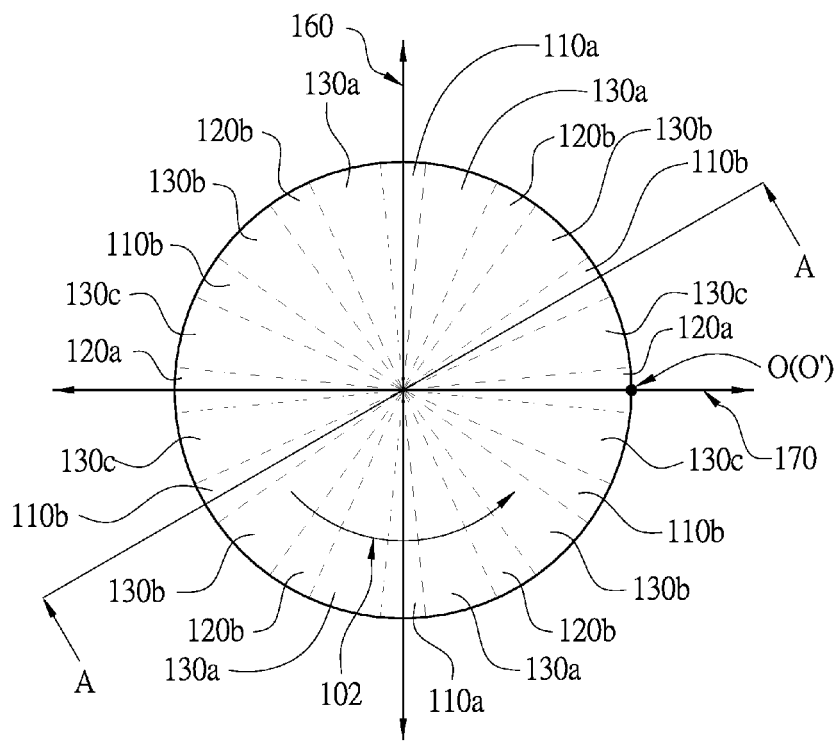
FIG. 16 is a schematic diagram of a progressive multifocal ophthalmic lens according to an eighth embodiment of the present invention.

FIG. 16 is a schematic diagram of a progressive multifocal ophthalmic lens according to an eighth embodiment of the present invention. The progressive multifocal ophthalmic lens of the present embodiment can be applied to a patient with presbyopia and astigmatism. The progressive multifocal ophthalmic lens includes a progressive multifocal surface and a toric surface. The progressive multifocal ophthalmic lens further includes at least three high power segments 110a, 110b, at least three low power segments 120a, 120b, and a plurality of progressive power segments 130a, 130b, 130c. Shapes of the high power segments 110a, 110b, the low power segments 120a, 120b, and the progressive power segments 130a, 130b, 130c are sectors. The high power segments 110a, 110b and the low power segments 120a, 120b are disposed alternately along an arc direction 102 of the progressive multifocal ophthalmic lens. The high power segments 110a, 110b, the low power segments 120a, 120b, and the progressive power segments 130a, 130b, 130c form the progressive multifocal surface. Two sides of each of the progressive power segments 130a, 130b, 130c along the arc direction 102 respectively connect one of the high power segments 110a, 110b and one of the low power segments 120a, 120b. The progressive multifocal ophthalmic lens of the present embodiment is a simultaneous visual lens, that is, images with different focuses can be simultaneously projected onto the retina through the high power segments 110a, 110b, the low power segments 120a, 120b, and the progressive power segments 130a, 130b, 130c. The human vision system or the brain selects clear images while excluding blurred images to achieve a zooming effect. The progressive multifocal ophthalmic lens mentioned above can be a contact lens or an intraocular lens, and the claimed scope is not limited in this respect.

Moreover, the toric surface has two orthogonal axes 160 and 170. The radii of curvature of the axes 160 and 170 are different from each other. The axis 160 can be used to correct eye ametropia, the axis 170 can be used to correct astigmatism.

The aforementioned progressive multifocal surface and the toric surface define the high power segments 110a, 110b, low power segments 120a, 120b, and the progressive power segments 130a, 130b, 130c according to the height variation thereof. There can be no boundaries between the adjacent progressive power segment 130a (or 130b, 130c) and the high power segment 110a (or 110b), and between the adjacent progressive power segment 130 (or 130b, 130c) and the low power segment 120a (or 120b).

In one or more embodiments, the cross-sectional view taken along line A-A of FIG. 16 can be the same as the cross-sectional view taken along line A-A of FIG. 1. That is, the cross-sectional view of FIG. 16 can be represented by FIG. 2A or 2B. Taking FIG. 2A as an example, the present embodiment of the progressive multifocal ophthalmic lens has two main surfaces 104 and 106 opposite to each other. The main surface 106 can contact the cornea if the progressive multifocal ophthalmic lens is a contact lens. As shown in FIG. 2A, the progressive multifocal ophthalmic lens can be a concave lens; as shown in FIG. 2B, the progressive multifocal ophthalmic lens can be a convex lens. The power of the progressive multifocal ophthalmic lens can be determined by the radii of curvature of the main surfaces 104 and 106 and the material and the thickness of the progressive multifocal ophthalmic lens.

In one or more embodiments, the progressive multifocal surface and the toric surface form a compound curved surface disposed at a main surface of the progressive multifocal ophthalmic lens, and the other main surface is a spherical surface or an aspherical surface. In other words, the compound curved surface is a superposition of the progressive multifocal surface and the toric surface. For example, the compound curved surface can be disposed at the main surface 104, and the main surface 106 can be a spherical surface or an aspherical surface; or the compound curved surface can be disposed at the main surface 106, and the main surface 104 can be a spherical surface or an aspherical surface.

Table 10 is power values of the progressive multifocal ophthalmic lens of FIG. 16 according to two examples, and the unit of the power is D (diopter). The power values of Set A can be applied to correct myopia presbyopia and astigmatism, and the power values of Set B can be applied to correct hyperopia presbyopia and astigmatism. In one or more examples, $\Delta d_1 = \Delta d_2 = +0.1$ D, and the claimed scope is not limited in this respect.

TABLE 10

The power values of the high power segments 110a, 110b, the low power segments 120a, 120b, and the progressive power segments 130a, 130b, 130c

|  | Set A | Set B |
|---|---|---|
| High power segments 110a | −5.5 D~−5.5 D + $\Delta d_1$ | +1.5 D~+1.5 D + $\Delta d_1$ |
| Low power segments 120a | −3.5 D~−3.5 D − $\Delta d_1$ | +3.5 D~+3.5 D − $\Delta d_1$ |
| High power segments 110b | −5.0 D~−5.0 D + $\Delta d_2$ | +2.0 D~+2.0 D + $\Delta d_2$ |
| Low power segments 120b | −4.0 D~−4.0 D − $\Delta d_2$ | +3.0 D~+3.0 D − $\Delta d_2$ |
| Progressive power segments 130a | −5.5 D + $\Delta d_1$~−4.0 D − $\Delta d_2$ | +1.5 D + $\Delta d_1$~+3.0 D − $\Delta d_2$ |
| Progressive power segments 130b | −4.0 D − $\Delta d_2$~−5.0 D + $\Delta d_2$ | +3.0 D − $\Delta d_2$~+2.0 D + $\Delta d_2$ |
| Progressive power segments 130c | −5.0 D + $\Delta d_2$~−3.5 D − $\Delta d_1$ | +2.0 D + $\Delta d_2$~+3.5 D − $\Delta d_1$ |

Figure 17:
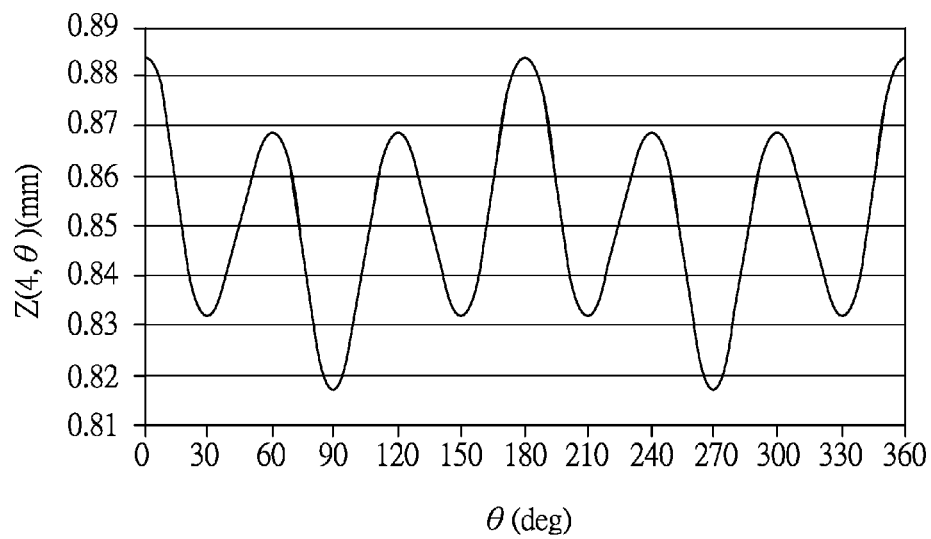
FIG. 17 is a graph of height coordinate Z from point O of FIG. 16 along the arc direction according to one example.

Reference is made to FIG. 17. The progressive multifocal surface and the toric surface form a compound curved surface disposed at a main surface of the progressive multifocal ophthalmic lens, and the other main surface is a spherical surface or an aspherical surface. FIG. 17 is a graph of height coordinate Z from point O of FIG. 16 along the arc direction 102 according to one example. As shown in FIG. 17, the height coordinate Z varies as there is an increase in the angular coordinate 8. Different height coordinates Z correspond to different segments. The center of the high power segments 110a are at 90° and 270°, respectively. The center of the low power segments 120a are at 0° and 180°, respectively. The center of the high power segments 110b are at 30°, 150°, 210°, and 330°, respectively. The center of the low power segments 120b are at 60°, 120°, 240°, and 300°, respectively. The center of the progressive power segments 130a are at 75°, 105°, 255°, and 285°, respectively. The center of the progressive power segments 130b are at 45°, 135°, 225°, and 315°, respectively. The center of the progressive power segments 130c are at 15°, 165°, 195°, and 345°, respectively.

In one or more embodiments, the progressive multifocal surface and the toric surface can be respectively disposed at two main surfaces of the progressive multifocal ophthalmic lens. For example, the progressive multifocal surface can be disposed at the main surface 104 (see FIG. 2A or 2B), and the toric surface can be disposed at the main surface 106 (see FIG. 2A or 2B); or the progressive multifocal surface is disposed at the main surface 106, and the toric surface is disposed at the main surface 104.

Figure 18A:
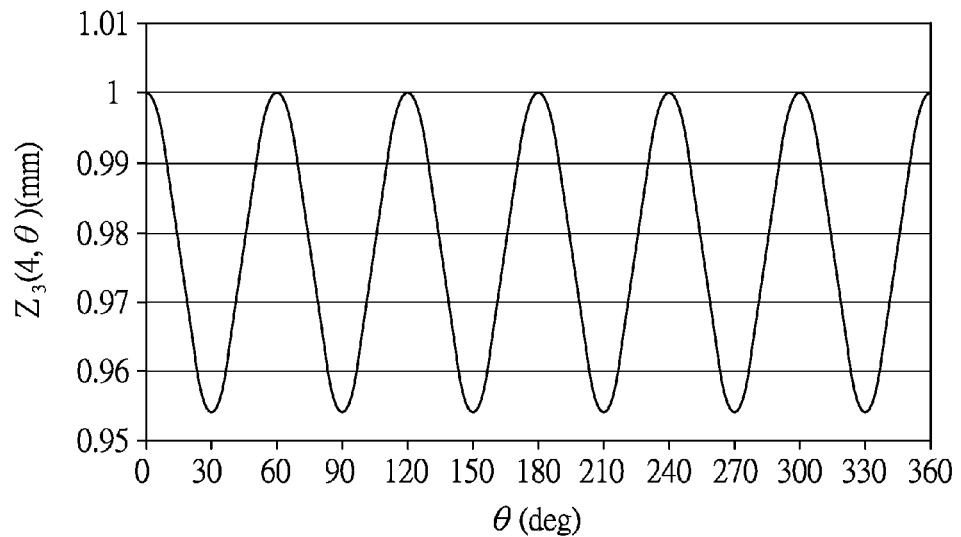
FIG. 18A is a graph of height coordinate $Z_3$ from point O of FIG. 16 along the arc direction according to one example.
Figure 18B:
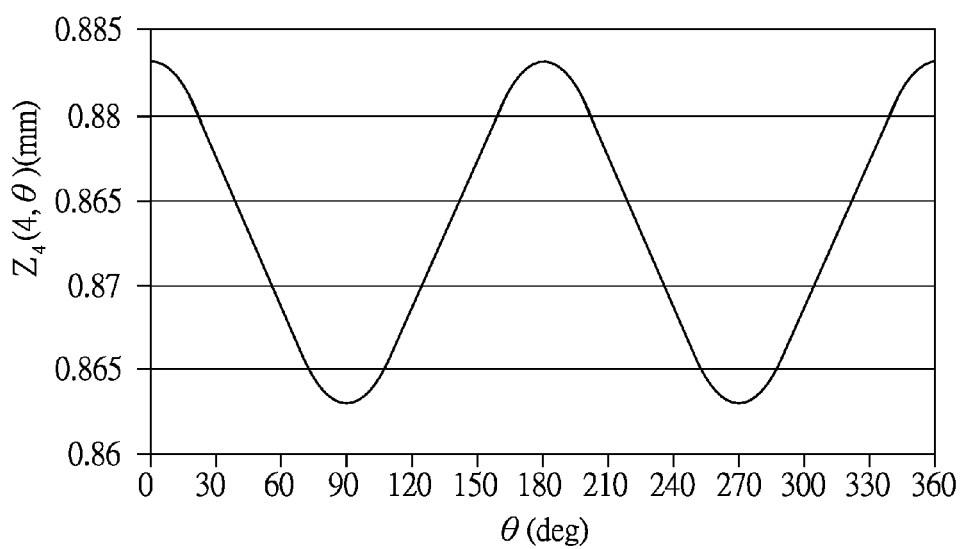
FIG. 18B is a graph of height coordinate $Z_4$ from point O' of FIG. 16 along the arc direction according to one example.

Reference is made to FIGS. 18A and 18B. The progressive multifocal surface and the toric surface are respectively disposed at two main surfaces of the progressive multifocal ophthalmic lens. FIG. 18A is a graph of height coordinate $Z_3$ from point O of FIG. 16 along the arc direction 102 according to one example, where the radial coordinate r of point O is 4 mm. FIG. 18B is a graph of height coordinate $Z_4$ from point O' of FIG. 16 along the arc direction 102 according to one example, where the radial coordinate r of point O' is 4 mm. As shown in FIG. 18A, the height coordinate $Z_3$ varies according to the progressive multifocal surface, and varies as there is an increase of the angular coordinate $\theta$. Moreover, the height coordinate $Z_4$ varies according to the toric surface, and varies as there is an increase of the angular coordinate $\theta$. Different combinations of the height coordinates $Z_3$ and $Z_4$ correspond to different segments.

The progressive multifocal ophthalmic lens mentioned above can be applied to patients with presbyopia and astigmatism. That is, a single progressive multifocal ophthalmic lens can correct presbyopia and astigmatism simultaneously. Moreover, although the size of the pupil changes with ambient light intensity, contrast, or age of the patient, with regards to the progressive multifocal ophthalmic lens of the present embodiment, the areas that the pupil respectively overlaps the high power segments 110a, 110b, the low power segments 120a, 120b, and the progressive power segments 130a, 130b, 130c are increased or decreased at the same ratio. For the patient with astigmatism, the vision quality respectively provided by the spherical segments and the cylindrical segments can be the same, and for the patient with presbyopia, vision quality is not compromised or sacrificed from dilation of the pupil or the switch of focus between distance-viewing and near-viewing.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A progressive multifocal ophthalmic lens, comprising:
at least three high power segments, at least three low power segments, and a plurality of progressive power segments, shapes of the high power segments and the low power segments are sectors, the high power segments and the low power segments are disposed alternately along an arc direction of the progressive multifocal ophthalmic lens, shapes of the progressive power segments are sectors, two sides of each of the progressive power segments along the arc direction respectively connect one of the high power segments and one of the low power segments, wherein the high power segments, the low power segments, and the progressive power segments form a progressive multifocal surface satisfying the following relationships:

when $\lfloor 180° \cdot (2s-2) \rfloor / p < \theta < \lfloor 180° \cdot (2s-1) \rfloor / p$, $$Z_1(r, \theta) = R - \sqrt{R^2 - r^2} + \left(\sum_{n=1}^{m} a_n \cdot r^n\right) \cdot \left[\cos\left[\pi \cdot \left(\frac{p \cdot \theta}{180}\right)^q\right] - 1\right]; \text{ and}$$

when $\lfloor 180° \cdot (2s-1) \rfloor / p < \theta < (180° \cdot 2s) / p$, $$Z_2(r, \theta) = R - \sqrt{R^2 - r^2} + \left(\sum_{n=1}^{m} a_n \cdot r^n\right) \cdot \left[\cos\left[\pi \cdot \left(2 - \frac{p \cdot \theta}{180}\right)^q\right] - 1\right],$$

wherein r is a radial coordinate of the progressive multifocal surface, $0 \leq r \leq r_0$, $r_0$ is a radius of an optical segment of the progressive multifocal surface, $\theta$ is an angular coordinate of the progressive multifocal surface, $0° \leq \theta \leq 360°$, $Z_1$ and $Z_2$ are height coordinates of the progressive multifocal surface from a reference plane, R is a radius of curvature of the progressive multifocal surface, p is a number of the high power segments or a number of the low power segments, wherein p is an integer greater than or equal to 3, q is a real number greater than or equal to 1, m and n are positive integers, $a_n$ is a real number, and s is an integer and $1 \leq s \leq p$.

2. The progressive multifocal ophthalmic lens of claim 1, wherein q=1.

3. The progressive multifocal ophthalmic lens of claim 1, further comprising:
a circular segment disposed at a center of circle of the progressive multifocal surface, the high power segments, the low power segments, the progressive power segments, and the circular segment forming the progressive multifocal surface,
wherein the progressive multifocal surface further satisfies the following relationships:

when $0 < r < r_1$, and $\lfloor 180° \cdot (2s-2) \rfloor / p < \theta < \lfloor 180° \cdot (2s-1) \rfloor / p$, $a_n$ are 0, and $R = R_1$;

when $0 < r < r_1$, and $\lfloor 180° \cdot (2s-1) \rfloor / p < \theta < (180° \cdot 2s) / p$, $a_n$ are 0, and $R = R_1$;

when $r_1 < r < r_0$, and $\lfloor 180° \cdot (2s-2) \rfloor / p < \theta < \lfloor 180° \cdot (2s-1) \rfloor / p$, q=1, and $R = R_2$; and when $r_1 < r < r_0$, and $\lfloor 180° \cdot (2s-1) \rfloor / p < \theta < (180° \cdot 2s) / p$, q=1, and $R = R_2$, wherein $r_1$ is a radius of the circular segment, $r_0$ is the radius of the optical segment of the progressive multifocal surface, $R_1$ is a radius of curvature of the circular segment, $R_2$ is a radius of curvature of the high power segments or the low power segments, and $Z_1(r, \theta)$ and $Z_2(r, \theta)$ are smoothly connected to each other at $r = r_1$.

4. A progressive multifocal ophthalmic lens, comprising:
at least three high power segments, at least three low power segments, and a plurality of progressive power segments, shapes of the high power segments and the low power segments are sectors, the high power segments and the low power segments are disposed alternately along an arc direction of the progressive multifocal ophthalmic lens, shapes of the progressive power segments are sectors, two sides of each of the progressive power segments along the arc direction respectively connect one of the high power segments and one of the low power segments, wherein the high power segments, the low power segments, and the progressive power segments form a progressive multifocal surface satisfying the following relationships:

when $\lfloor 180° \cdot (2s-2) \rfloor / p < \theta < \lfloor 180° \cdot (2s-1) \rfloor / p$, $$Z_1(r, \theta) = R - \sqrt{R^2 - r^2} - \left(\sum_{n=1}^{m} a_n \cdot r^n\right) \cdot \left[\cos\left[\pi \cdot \left(1 - \frac{p \cdot \theta}{180}\right)^q\right] + 1\right]; \text{ and}$$

when $\lfloor 180° \cdot (2s-1) \rfloor / p < \theta < (180° \cdot 2s) / p$, $$Z_2(r, \theta) = R - \sqrt{R^2 - r^2} - \left(\sum_{n=1}^{m} a_n \cdot r^n\right) \cdot \left[\cos\left[\pi \cdot \left(\frac{p \cdot \theta}{180} - 1\right)^q\right] + 1\right],$$

wherein r is a radial coordinate of the progressive multifocal surface, $0 \leq r \leq r_0$, $r_0$ is a radius of an optical segment of the progressive multifocal surface, $\theta$ is an angular coordinate of the progressive multifocal surface, $0° \leq \theta \leq 360°$, $Z_1$ and $Z_2$ are height coordinates of the progressive multifocal surface from a reference plane, R is a radius of curvature of the progressive multifocal surface, p is a number of the high power segments or a number of the low power segments, wherein p is an integer greater than or equal to 3, q is a real number greater than or equal to 1, m and n are positive integers, $a_n$ is a real number, and s is an integer and $1 \leq s \leq p$.

5. The progressive multifocal ophthalmic lens of claim 4, wherein q=1.

6. The progressive multifocal ophthalmic lens of claim 4, further comprising:
   a circular segment disposed at a center of circle of the progressive multifocal surface, the high power segments, the low power segments, the progressive power segments, and the circular segment forming the progressive multifocal surface,
   wherein the progressive multifocal surface further satisfies the following relationships:

when $0 < r < r_1$, and $\lfloor 180° \cdot (2s-2) \rfloor / p < \theta < \lfloor 180° \cdot (2s-1) \rfloor / p$, $a_n$ are 0, and $R = R_1$;

when $0 < r < r_1$, and $\lfloor 180° \cdot (2s-1) \rfloor / p < \theta < (180° \cdot 2s)/p$, $a_n$ are 0, and $R = R_1$;

when $r_1 < r < r_0$, and $\lfloor 180° \cdot (2s-2) \rfloor / p < \theta < \lfloor 180° \cdot (2s-1) \rfloor / p$, q=1, and $R = R_2$; and when $r_1 < r < r_0$, and $\lfloor 180° \cdot (2s-1) \rfloor / p < \theta < (180° \cdot 2s)/p$, q=1, and $R = R_2$, wherein $r_1$ is a radius of the circular segment, $r_0$ is the radius of the optical segment of the progressive multifocal surface, $R_1$ is a radius of curvature of the circular segment, $R_2$ is a radius of curvature of the high power segments or the low power segments, and $Z_1(r, \theta)$ and $Z_2(r, \theta)$ are smoothly connected to each other at $r = r_1$.

7. A progressive multifocal ophthalmic lens, comprising:
   a progressive multifocal surface and a toric surface, wherein the progressive multifocal ophthalmic lens further comprises:
   at least three high power segments, at least three low power segments, and a plurality of progressive power segments, shapes of the high power segments and the low power segments are sectors, the high power segments and the low power segments are disposed alternately along an arc direction of the progressive multifocal ophthalmic lens, shapes of the progressive power segments are sectors, two sides of each of the progressive power segments along the arc direction respectively connect one of the high power segments and one of the low power segments, wherein the high power segments, the low power segments, and the progressive power segments form the progressive multifocal surface satisfying the following relationships when $\lfloor 180° \cdot (2s-2) \rfloor / p < \theta < \lfloor 180° \cdot (2s-1) \rfloor / p$, $$Z_1(r, \theta) = R - \sqrt{R^2 - r^2} + \left(\sum_{n=1}^{m} a_n \cdot r^n\right) \cdot \left[\cos\left[\pi \cdot \left(\frac{p \cdot \theta}{180}\right)^q\right] - 1\right]; \text{ and}$$

when $\lfloor 180° \cdot (2s-1) \rfloor / p < \theta < (180° \cdot 2s)/p$, $$Z_2(r, \theta) = R - \sqrt{R^2 - r^2} + \left(\sum_{n=1}^{m} a_n \cdot r^n\right) \cdot \left[\cos\left[\pi \cdot \left(2 - \frac{p \cdot \theta}{180}\right)^q\right] - 1\right],$$

wherein r is a radial coordinate of the progressive multifocal surface, $0 \leq r \leq r_0$, $r_0$ is a radius of an optical segment of the progressive multifocal surface, $\theta$ is an angular coordinate of the progressive multifocal surface, $0° \leq \theta \leq 360°$, $Z_1$ and $Z_2$ are height coordinates of the progressive multifocal surface from a reference plane, R is a radius of curvature of the progressive multifocal surface, p is a number of the high power segments or a number of the low power segments, wherein p is an integer greater than or equal to 3, q is a real number greater than or equal to 1, m and n are positive integers, $a_n$ is a real number, and s is an integer and $1 \leq s \leq p$.

8. The progressive multifocal ophthalmic lens of claim 7, wherein the progressive multifocal surface and the toric surface form a compound curved surface disposed at a main surface of the progressive multifocal ophthalmic lens, and the other main surface is a spherical surface or an aspherical surface.

9. The progressive multifocal ophthalmic lens of claim 7, wherein the progressive multifocal surface and the toric surface are respectively disposed at two main surfaces of the progressive multifocal ophthalmic lens.

* * * * *